US008486431B2

(12) United States Patent
Ogata

(10) Patent No.: US 8,486,431 B2
(45) Date of Patent: Jul. 16, 2013

(54) METHOD OF CONTROLLING FLOATING VIRUS INFECTION

(75) Inventor: Norio Ogata, Osaka (JP)

(73) Assignee: Taiko Pharmaceutical Co., Ltd., Osaka (JP)

( * ) Notice: Subject to any disclaimer, the term of this patent is extended or adjusted under 35 U.S.C. 154(b) by 117 days.

(21) Appl. No.: 12/085,553

(22) PCT Filed: Nov. 27, 2006

(86) PCT No.: PCT/JP2006/323581

§ 371 (c)(1), (2), (4) Date: Nov. 3, 2008

(87) PCT Pub. No.: WO2007/061092

PCT Pub. Date: May 31, 2007

(65) Prior Publication Data

US 2009/0053325 A1 Feb. 26, 2009

(30) Foreign Application Priority Data

Nov. 28, 2005 (JP) ................................ 2005-342503

(51) Int. Cl.

| | |
|---|---|
| ***A01N 25/00*** | (2006.01) |
| ***A01N 59/00*** | (2006.01) |
| ***A61L 9/015*** | (2006.01) |
| ***A61L 2/20*** | (2006.01) |
| ***A61K 33/20*** | (2006.01) |

(52) U.S. Cl.

USPC .......... 424/405; 422/1; 422/4; 422/9; 422/28; 422/37; 424/661

(58) Field of Classification Search

None

See application file for complete search history.

(56) References Cited

U.S. PATENT DOCUMENTS

| | | | |
|---|---|---|---|
| 6,077,495 | A | 6/2000 | Speronello et al. |
| 6,363,734 | B1 | 4/2002 | Aoyagi |
| 2003/0230492 | A1 | 12/2003 | Kadlec et al. |
| 2005/0095170 | A1 | 5/2005 | Speronello et al. |

FOREIGN PATENT DOCUMENTS

| | | | |
|---|---|---|---|
| CN | 2662908 | Y | 12/2004 |
| JP | 63-12226 | A | 1/1988 |
| JP | 2002-272827 | A | 9/2002 |
| WO | WO 03/047640 | * | 6/2003 |

OTHER PUBLICATIONS

Junli et al. (Wat. Res. 1997, 31(3): 455-460).*

Schooley et al. (J Infect Dis 2007, 195(6): 770-772).*

Wang et al. (Journal of Virological Methods 2005, 126, 171-177).*

"Enviroment Disinfection of Dissection Room," Sterilization/Disinfection Manual, Nov. 1, 1991, Sterilization/Disinfection Manual Compiling Committee, Ishiyaku Publishing Inc., and English translation of Technical Notes.

English Translation of International Preliminary Report on Patentability for corresponding Application No. PCT/JP2006/323581.

(Continued)

*Primary Examiner* — Ernst Arnold

(74) *Attorney, Agent, or Firm* — Osha Liang LLP

(57) ABSTRACT

A method of controlling floating virus infection. The method includes the step of: supplying chlorine dioxide gas into a space where floating virus can be present by a gas concentration which allows the animal to live or stay, but deactivates the virus.

8 Claims, 1 Drawing Sheet

OTHER PUBLICATIONS

Supplementary Extended European Search Report issued Jan. 18, 2010, by the European Patent Office (Munich), in related European Application No. 06833385.5 (4 pages).

Office Action issued May 25, 2012, by the China Patent Office in corresponding Chinese Patent Application CN 2006-80044049.0 (4 pages).

Ying, Hui-fang, et al., "Observation of efficacy and effectual time in three kinds of air disinfection method"; 1994-2012 China Academic Journal Electronic Publishing House, Jun. 21, 2005; pp. 643-645.

Application of Chlorine Dioxide in Hospital as a Disinfectant; 1994-2012 China Academic Journal Electronic Publishing House; pp. 268-269.

Office Action dated Jun. 2, 2011, issued by the Chinese Patent Office in related Chinese Patent Application No. CN-200680044049.0 (4 pages).

Office Action dated Aug. 21, 2012, issued by the Canadian Intellectual Property Office in related Canadian Patent Application No. 2,632,253 (3 pages).

Wang, Li, et al., "Inactivation effect of chlorine dioxide on influenza viruses in water"; China Environmental Science, vol. 21(3), 2001; pp. 256-258, with English translation (6 pages).

Office Action dated Apr. 16, 2013, from the Japan Patent Office in related Japanese Patent Application No. 2007-546522 (4 pages).

T. Iwaki, et al., "Sterilization of the Biological Safety Cabinet Using Chlorine Dioxide"; Jikeikai Medical Journal, vol. 120, No. 6, Nov. 15, 2005; pp. 212-213, with partial English translation (3 pages).

* cited by examiner

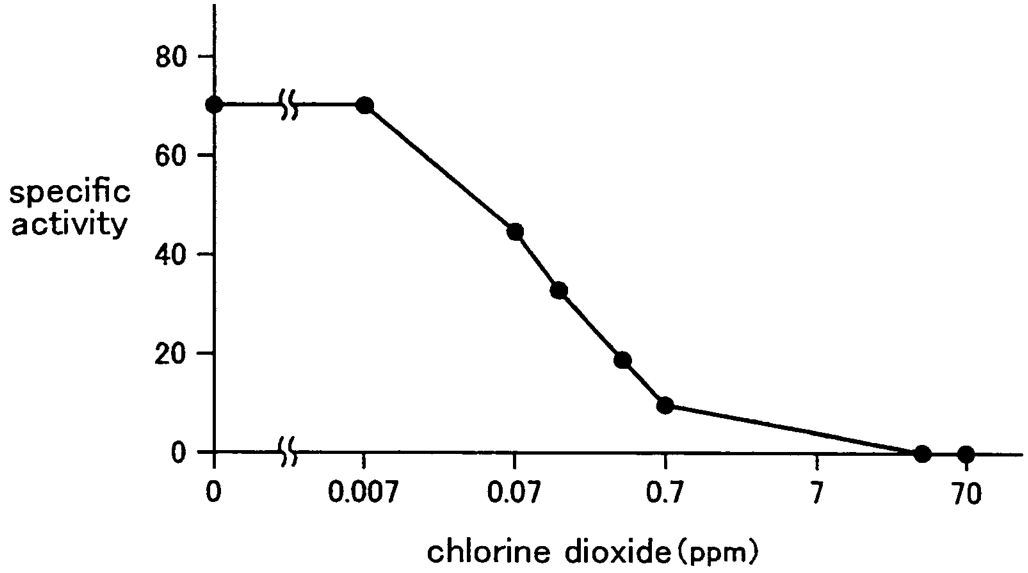
80
60
40
20
0
specific activity
0
0.007
0.07
0.7
7
70
chlorine dioxide (ppm)

METHOD OF CONTROLLING FLOATING VIRUS INFECTION

CROSS REFERENCE TO RELATED APPLICATIONS

This is a national stage application of PCT/JP2006/323581, filed on Nov. 27, 2006, which claims priority of Japanese application No. 2005-342503, filed on Nov. 28, 2005. The disclosures of these prior applications are incorporated by reference in their entirety.

TECHNICAL FIELD

The present invention relates to a method of controlling floating virus infection.

BACKGROUND ART

In case e.g. a worker infected with a certain type of respiratory virus is present in an office or the like, there is the risk of infection with the same respiratory virus for the other workers working within the same office. In such case, such infected workers may develop poor physical condition and experience eventual onset of the respiratory organ viral disease, thus leading to significant deterioration in the working efficiency in that office.

Here, the term respiratory virus, is a generic name for various viruses which cause respiratory diseases such as pneumonia in animals. Among them are included influenza virus, parainfluenza virus, rhinovirus, bird flu virus, SARS virus, corona virus, etc. Infection with such respiratory virus and subsequent onset of respiratory virus disease can sometimes result in death of the subject.

Such respiratory viruses exist also in droplets exhaled from a respiratory organ of the infected subject. As the droplets can float in the air, inhalation of droplets containing the respiratory virus leads to spread of the infection and the spread of the respiratory virus.

Incidentally, though not commonly called "respiratory viruses", measles virus and rubella virus belong in the same category as above because inhalation by an un-infected subject of air contaminated with droplets from a respiratory organ of an infected subject causes secondary infection through the respiratory organ of the former.

For preventing spreading of respiratory virus, one effective measure is eliminating and/or deactivating the respiratory virus floating in the room (in the air). As one example of a method of deactivating respiratory virus floating in a room, there is a method called fumigation (see Non-Patent Document 1).

Non-Patent Document: "Sterilization/Disinfection Manual", Ishiyaku Publishing Inc. 1991, Sterilization/Disinfection Manual Compiling Committee.

DISCLOSURE OF THE INVENTION

Object to be Achieved by Invention

Fumigation is a method wherein a hermetically closed room is filled with a gas prepared by evaporating an agent so as to kill insects, mites, fungus present inside the room. Some examples of the agent employed for fumigation are formalin, methyl bromide, aluminum phosphide, cyanide fume, etc.

However, such agents employed for fumigation are very poisonous for living bodies. So, during fumigation process, workers need to stop their works and evacuate from inside the room, thus leading to deterioration in the working efficiency.

The present invention has been made in view of the above-described state of the art. The invention provides a method of controlling floating virus infection, capable of preventing e.g. virus infection to an animal while the animal is allowed to live or stay safely inside a space where the animal is present and viruses are floating.

Means to Achieve the Object

According to a first characterizing feature of the inventive method of controlling floating virus infection for achieving the above-noted object, the method comprises the step of supplying chlorine dioxide gas into a space where floating virus can be present by a gas concentration which allows the animal to live or stay, but deactivates the virus.

Chlorine dioxide gas has strong oxidative power and sterilizing power as well as strong virus deactivating power. For this reason, by exposing the floating virus to chlorine dioxide gas, the floating virus can be deactivated.

In this specification, the term "deactivation" refers to a condition of e.g. floating virus being destroyed, thus becoming unable to proliferate in a host, or a condition of the floating virus being still active, but hardly capable of proliferation in a host.

Therefore, if chlorine dioxide gas is supplied to a certain space and the concentration of the gas within the space is maintained at such a concentration as to deactivate the floating virus, even if floating virus is newly introduced into the space, this floating virus can be deactivated immediately. Accordingly, it is possible to prevent virus infection to the animal present within that space.

Moreover, as the concentration of chlorine dioxide within the space is such that the animal is allowed to live or stay, but the floating virus is deactivated, the animal can lead a normal living in the space. Therefore, it is possible to e.g. maintain air inside an office under the condition for deactivating floating virus, while allowing workers to continue work in this office. Consequently, secondary infection with the virus can be effectively prevented to allow the workers to maintain their health. And, also, there occurs no deterioration in the working efficiency since the work need not be suspended during an air cleaning operation by e.g. fumigation.

Incidentally, the term "animal" refers to any animal or living creature which lives or stays within the space and can be infected with the floating virus, including mammals such as humans, domestic livestock, birds, reptiles, etc.

According to a second characterizing feature of the present invention, the method comprises the step of supplying chlorine dioxide gas into a space where floating virus can be present by a gas concentration which allows the animal to live or stay, but can prevent infection of the animal with the virus.

With this characterizing construction, the floating virus loses its infectability, thus being incapable of inter-host infection. Here, the language "lose infectability" refers to such a condition where the floating virus experiences denaturation in its surface proteins required for host infection, so that the virus can no longer infect the host.

Therefore, inter-host infection can be prevented and the possibility of the animal's being infected with the floating virus and onset of viral disease associated therewith can be significantly reduced.

According to a third characterizing construction of the present invention, the method comprises the step of supplying chlorine dioxide gas into a space where floating virus can be present by a gas concentration which allows the animal to live or stay, but can prevent onset of viral disease in the animal infected with the virus.

With this characterizing construction, even if the animal is infected with the floating virus, the possibility of onset of viral disease in the infected animal can be reduced.

According to a fourth characterizing construction of the present invention, the method comprises the step of supplying chlorine dioxide gas into a space where floating virus can be present by a gas concentration which allows the animal to live or stay, but can treat the animal infected with the virus and with onset of the viral disease associated therewith.

With this characterizing construction, even if the animal is infected with the floating virus and the animal experiences subsequent onset of the viral disease, the symptoms of this disease can be alleviated and its contraction period can be shortened.

According to a fifth characterizing construction of the present invention, the concentration of the chlorine dioxide gas within the space is set from 0.0001 ppm to 0.1 ppm.

With this characterizing construction, if the concentration of the chlorine dioxide gas within the space is under 0.0001 ppm, it is difficult to deactivate the floating virus. Further, as the working environment standard value for chlorine dioxide is 0.1 ppm, a value greater than 0.1 ppm can be harmful for the animal. Therefore, by setting the chlorine dioxide gas concentration within the space at the extremely low concentration from 0.0001 ppm to 0.1 ppm, the floating virus can be deactivated and at the same time the animal can live or stay more safely in the space.

According to a sixth characterizing construction of the present invention, the floating virus comprises respiratory virus.

With this characterizing construction, prevention of respiratory virus infection and prevention and treatment of possible respiratory disease (e.g. pneumonia) which may develop after the infection can be effectively carried out.

According to a seventh characterizing construction of the present invention, the respiratory virus comprises influenza virus.

With this characterizing construction, prevention of influenza virus infection and prevention and treatment of various possible syndromes (e.g. fever attack, runny nose, sore throat, etc.) which may develop after the infection can be effectively carried out.

BEST MODE OF EMBODYING THE INVENTION

[Embodiments]

The present invention may be implemented with using an appropriate chlorine dioxide generator, for example.

Some non-limiting examples of chlorine dioxide generator suitable for the present invention include a large stationary apparatus, a small stationary apparatus, a small portable apparatus, and an instrument configured to charge a generating agent into gel or mix a dry agent therewith so as to generate a low concentration of chlorine dioxide gas for an extended period of time in a semi-automatic manner. However, the invention is not limited thereto, but it is also possible to employ an apparatus configured to discharge a low concentration of chlorine dioxide gas into a mouth.

The above chlorine dioxide generator apparatus comprises a reaction vessel, drug solution tanks capable of reserving respective drug solutions therein, liquid pumps, an air pump, a diluter, etc.

There are provided two kinds of drug solution tanks, each receiving therein chlorite water solution or acid therein. Some examples of chlorite usable are alkali metal chlorite (sodium chlorite, potassium chlorite, lithium chlorite), or alkali earth metal chlorite (calcium chlorite, magnesium chlorite, barium chlorite) . . . etc. However, the invention is not limited thereto.

Some examples of acid usable are inorganic acids including hydrochloric acid, sulfuric acid, nitric acid, phosphoric acid. However, the invention is not limited thereto.

The liquid pump is provided as accompanying the drug solution tank. The pump is capable of precision control of liquid feed by means of a timer.

By the liquid pump, predefined amounts of chlorite water solution and acid solution are sent into the reaction vessel periodically, in which the solutions are mixed and reacted with each other to generate chlorine dioxide gas. The chlorine dioxide gas thus generated is mixed in the diluter with a predetermined rate of air sent by the air pump to be diluted to a predetermined concentration (preferably, 0.8 ppm).

The diluted chlorine dioxide gas is then supplied into a desired space where floating viruses can be present and the concentration of the chlorine dioxide gas within this space is maintained at a concentration which allows an animal to live or stay, but deactivates the viruses.

This concentration can be a concentration capable of preventing infection of the animal with the floating virus, or a concentration capable of preventing onset of a viral disease in the animal infected with the floating virus, or a concentration capable of treating the animal which has been infected with the floating virus and in which the disease associated therewith has developed.

Specifically, based on results of influenza infection experiments using mice to be detailed later, this concentration is maintained to range from 0.05 ppm to 0.1 ppm.

Further, the concentration of chlorine dioxide can be set in the following manners for example. In the influenza infection experiment using mice to be described later, the mice were infected by administrating thereto a high concentration of virus greater than 10 $LD_{50}$. In general, when there occurs respiratory viral infectious disease within such a large structure as a theater, an extremely low concentration of virus can be a problem. For instance, even such low concentration thereof as low as 0.02 $LD_{50}$ can cause infection.

In the above situation, the virus concentration in the air is about 1/500 of the above-noted concentration (10 $LD_{50}$/0.02 $LD_{50}$). Therefore, the concentration of chlorine dioxide gas required for preventing influenza infection is 0.0001 ppm (0.05/500).

That is to say, according to the present invention, by using the chlorine dioxide generator described above, the concentration of chlorine dioxide inside the space is maintained at the extremely low concentration (0.0001 to 0.1 ppm). With this, it becomes possible to maintain the chlorine dioxide gas concentration at such a concentration which can constantly be safe for the animal and which can, at the same time, deactivate the floating virus or deprive it of its infectability.

(Space)

The space to which the present invention is applicable includes a space that people enter/exit, such as a theater, an airport lobby, a business office, a classroom, or a space where animals are raised or plants are grown such as a mouse cage, a vinyl house, etc. or even such a "space" as oral cavity of a human, etc. However, the invention is not limited thereto. The invention can be applied to any other desired space which can assume, as desired, a closed state or an opened state.

(Floating Virus)

The "floating virus" as used herein refers to any virus which can float inside the above-described space. Some examples thereof include respiratory viruses, such as influenza virus, parainfluenza virus, rhinovirus, bird flu virus, SARS virus, corona virus, RS virus, etc. However, the invention is not limited thereto. The present invention is applicable to prevention and/or treatment of measles virus and rubella virus as inhalation by an un-infected subject of air contaminated with droplets from a respiratory organ of an infected subject causes secondary infection through the respiratory organ of the former, although these are not commonly called "respiratory viruses".

(Animal)

The living creature or organism to which the present invention is applied includes any animal or living creature which lives or stays within the space and can be infected with the floating virus, including mammals such as humans, domestic livestock, birds, reptiles, etc.

EXAMPLES

Next, the present invention will be described in details with reference to some examples thereof. It is understood; however, that the present invention is not limited thereto.

(Generation of Chlorine Dioxide Gas)

0.25% sodium chlorite ($NaClO_2$) and 0.9% hydrochloric acid are charged and kept within separate drug solution tanks. Then, by using the liquid pump attached to each tank, each solution is sent to the reaction vessel.

Chlorine dioxide generated after the mixing and reaction between the sodium chlorite and hydrochloric acid is added with air introduced thereto and the resultant product is discharged as a gas. In this, the discharged chlorine dioxide gas had a concentration of about 50 ppm. The discharged chlorine dioxide gas was then mixed in the diluter with air of a predetermined flow rate to be diluted to a low concentration.

In this experiment, the diluted and discharged chlorine dioxide gas had a concentration of 0.8 ppm. As will be described later, inside a mouse cage, the gas will be further diluted to 0.08 ppm or lower. The concentrations of the chlorine dioxide gases were determined always by a chlorine dioxide meter (4330-SP, Interscan Corporation, U.S.A.)

(Preparation of Influenza Virus)

The influenza virus employed was prepared and obtained by proliferating Type A influenza strain A/PR8 (H1N1) in a culture medium containing 2% bovine fetal serum, with using, as a host, MDCK cell (ATCC CCL34) which is canine renal cell.

The viruses proliferated as above were suspended in a phosphate buffer solution (PBS) and then rendered into aerosol for subsequent use. In the above, the concentration of the suspended virus was adjusted to be 10, 100 or 1000 times of the concentration ($LD_{50}$) which, if introduced as aerosol into the mouse cage, would kill 50% of mice, respectively.

(Animal Experiment)

Animal experiment was conducted with using 8-week old male CD-1 mice. Fifteen mice, as one group, were put into a mouse cage dimensioned as: 25.5 cm×36.8 cm×8.0 cm. Into this, the aerosol of Type A influenza was introduced at the rate of 12.5 liter per minute.

In the above, at the same time, chlorine dioxide gas at 0.8 ppm concentration was fed at the flow rate of 0.6 to 1.8 liter per minute. The chlorine dioxide gas present within the mouse cage was diluted by the aerosol present therein.

In this experiment, concentration settings of 0 ppm, 0.03 ppm, 0.05 ppm and 0.08 ppm, as actually determined within the mouse cage, were possible for the chlorine dioxide gas. Data at these four kinds of concentration were obtained.

The exposure period for the mice to the virus aerosol was set to 15 minutes.

In principle, the introduction of chlorine dioxide gas was effected simultaneously with the introduction of the virus-containing aerosol. In some of the experiments, however, the introduction of chlorine dioxide gas was effected with delays relative to the introduction of the virus-containing aerosol. This was done in order to check whether the chlorine dioxide gas can prevent onset of viral disease resulting from the virus which has entered the lungs already.

As a control experiment, a phosphate buffer solution not containing any virus was employed and aerosol of this phosphate buffer solution was introduced into the mouse cage.

For those mice after the virus exposure, one mouse after another thereof was put into a separate mouse cage and kept therein in isolation for two weeks. During this period, in order to check presence/absence of virus infection and degree thereof (the number of virus), lung tissues were excised from five of the total fifteen mice.

The excised lungs were ground/crushed and then viruses were separated therefrom and the amount thereof was quantified.

For this quantification of the viruses within the lung, the crushed lung substance was suspended and its dilution series were prepared temporarily. Then, these were infected to the culture cells and $TCID_{50}$ values (50% tissue culture infection amount) were obtained.

On the other hand, as to the remaining 10 mice, life or death thereof was observed until day 14. During this period, if a mouse died in this period, its lung tissue was excised therefrom and fixed in formalin at that timing. If a mouse did not die in this period, then, its tissue was excreted and fixed in formalin on day 14. And, histophathologic analysis was conducted thereon by the standard method.

(Simultaneous Administration of 0.08 ppm Chlorine Dioxide Gas)

Mice were exposed to aerosol containing 1000 $LD_{50}$ virus for 15 minutes and to these mice, chlorine dioxide gas at 0.08 ppm concentration (final concentration inside the mouse cage) was administered simultaneously. The life and death of these mice are shown below (Table 1)

TABLE 1

| | Number of mice which died after exposure to virus (data for 10 mice in each group) | | | | | | |
|---|---|---|---|---|---|---|---|
| | days after exposure | | | | | | |
| | 3 | 4 | 5 | 8 | 9 | 10 | 14 |
| 0 ppm group | 0 | 8 | 10 | 10 | 10 | 10 | 10 |
| 0.08 ppm group | 0 | 0 | 0 | 0 | 6 | 10 | 10 |

As may be apparent from Table 1 above, it may be understood that the deaths occurred with delay in the mice administered with the 0.08 ppm chlorine dioxide gas. On this difference, statistical significant difference test can be done. Its significance level (risk rate) was under 0.0001 ($P<0.0001$). That is, this difference was found to have "statistical significance".

Next, respecting the same experiment, from each 15 mice group 3 days after virus exposure, 5 mice were sampled from each group and their lung tissues were excreted and crushed and the virus contained therein was quantified (Table 2).

TABLE 2

Total virus amount in lung tissues on Day 3 ($TCID_{50}$ values)

| | serial mouse number | | | | |
|---|---|---|---|---|---|
| | 1 | 2 | 3 | 4 | 5 |
| 0 ppm group | $10^{7.8}$ | $10^{7.8}$ | $10^{7.3}$ | $10^{7.8}$ | $10^{7.8}$ |

| | serial mouse number | | | | |
|---|---|---|---|---|---|
| | 6 | 7 | 8 | 9 | 10 |
| 0.08 ppm group | $10^{6.3}$ | $10^{6.3}$ | $10^{6.8}$ | $10^{5.8}$ | $10^{6.8}$ |

As shown in Table 2, when the numbers of virus in all the tissues were represented as $TCID_{50}$ values, the average value of the 0 ppm group was $10^{7.7}$, and the average value of the 0.08 ppm administration group was $10^{6.4}$, respectively. That is to say, the values of the group administered with the 0.08 ppm chlorine dioxide gas was only 5% of that of the control group (0 ppm group) (note the values are represented in the logarithm system).

Based on the above, it is believed that in the presence of chlorine dioxide gas, proliferation of virus was restricted or the amount of virus having infectability at the time of infection was small.

These conditions can be interpreted to be a condition where the floating viruses lost activity and could hardly proliferate in the bodies of mice or a condition where the infection to the mice was prevented due to insufficient infectability of the floating viruses.

From the above, it has been found that if influenza virus is present at the concentration of 1000 $LD_{50}$, inhibitory effect against onset of influenza can be obtained with administration of 0.08 ppm chlorine dioxide gas.

Subsequently to the above, a similar experiment was conducted with varying the concentration of virus to which mice were exposed.

In this experiment, aerosols of virus with concentrations of 10 $LD_{50}$ (10 times greater than $LD_{50}$) and 100 $LD_{50}$ (100 times greater than $LD_{50}$) were introduced to the mouse cages for 15 minutes; and at the same time, 0.08 ppm (final concentration inside the mouse cage) chlorine dioxide gas was introduced to the mouse cages.

As a result, in the case of the virus administered group with the 10 $LD_{50}$ virus concentration, no onset of influenza was found for 14 days in the group administered with 0.08 ppm chlorine dioxide. (Table 3).

TABLE 3

Number of mice which died after exposure to 10 $LD_{50}$ virus (data for 10 mice in each group)

| | days after exposure | | | | | | |
|---|---|---|---|---|---|---|---|
| | 3 | 4 | 5 | 8 | 9 | 10 | 14 |
| 0 ppm group | 0 | 0 | 0 | 5 | 7 | 10 | 10 |
| 0.08 ppm group | 0 | 0 | 0 | 0 | 0 | 0 | 0 |

Also, the amount of virus in the lungs of the mice on Day 3 after the virus exposure was clearly lower for the chlorine dioxide administered group. (Table 4)

TABLE 4

Total virus amount in lung tissues on Day 3 after 10 $LD_{50}$ virus exposure ($TCID_{50}$ values)

| | serial mouse number | | | | |
|---|---|---|---|---|---|
| | 21 | 22 | 23 | 24 | 25 |
| 0 ppm group | $10^{5}$ | $10^{5}$ | $10^{5.3}$ | $10^{5.1}$ | $10^{5}$ |

| | serial mouse number | | | | |
|---|---|---|---|---|---|
| | 26 | 27 | 28 | 29 | 210 |
| 0.08 ppm group | $10^{3}$ | $10^{3.2}$ | $10^{3.3}$ | $10^{3}$ | $10^{3.1}$ |

Further, in the virus administered group with 100 $LD_{50}$ virus concentration too, no onset of influenza after the virus exposure was found (Table 5) and the virus amount in the lung (Table 6) was small for the chlorine dioxide gas administered group.

TABLE 5

Number of mice which died after exposure to 100 $LD_{50}$ virus (data for 10 mice in each group)

| | days after exposure | | | | | | |
|---|---|---|---|---|---|---|---|
| | 3 | 4 | 5 | 8 | 9 | 10 | 14 |
| 0 ppm group | 0 | 0 | 3 | 6 | 8 | 10 | 10 |
| 0.08 ppm group | 0 | 0 | 0 | 0 | 0 | 0 | 0 |

TABLE 6

Total virus amount in lung tissues on Day 3 after 100 $LD_{50}$ virus exposure ($TCID_{50}$ values)

| | serial mouse number | | | | |
|---|---|---|---|---|---|
| | 31 | 32 | 33 | 34 | 35 |
| 0 ppm group | $10^{6.3}$ | $10^{6.2}$ | $10^{6.1}$ | $10^{6.1}$ | $10^{6.6}$ |

| | serial mouse number | | | | |
|---|---|---|---|---|---|
| | 36 | 37 | 38 | 39 | 310 |
| 0.08 ppm group | $10^{5.5}$ | $10^{5.8}$ | $10^{5.6}$ | $10^{5.7}$ | $10^{5.9}$ |

From the above, it has been found that in the cases of influenza virus being present at the concentrations of 10 $LD_{50}$ and 100 $LD_{50}$, sufficient inhibitory effect against onset of influenza can be obtained with administration of 0.08 ppm chlorine dioxide gas.

(Simultaneous Administration of 0.05 ppm Chlorine Dioxide)

Next, regarding the case of administration of 10 $LD_{50}$ concentration virus, investigation was made on the effect of simultaneous administration of an even lower concentration (0.05 ppm) of chlorine dioxide. The result showed that no onset of influenza was found in the group of chlorine dioxide administered group (Table 7) and the virus amount in the lung (Table 8) was small.

From the above, it has been found that in the cases of influenza virus being present at the concentrations of 10

$LD_{50}$, onset of influenza can be inhibited with simultaneous administration of 0.05 ppm chlorine dioxide gas.

TABLE 7

Number of mice which died after exposure to 10 $LD_{50}$ virus with simultaneous administration of 0.05 ppm chlorine dioxide (data for 10 mice in each group)

| | days after exposure | | | | | | |
|---|---|---|---|---|---|---|---|
| | 3 | 4 | 5 | 8 | 9 | 10 | 14 |
| 0 ppm group | 0 | 0 | 4 | 5 | 8 | 10 | 10 |
| 0.05 ppm group | 0 | 0 | 0 | 0 | 0 | 0 | 0 |

TABLE 8

Total virus amount in lung tissues on Day 3 after 10 $LD_{50}$ virus exposure with simultaneous administration of 0.05 ppm chlorine dioxide ($TCID_{50}$ values)

| | serial mouse number | | | | |
|---|---|---|---|---|---|
| | 41 | 42 | 43 | 44 | 45 |
| 0 ppm group | $10^{6.2}$ | $10^{6.5}$ | $10^{6.2}$ | $10^{6.2}$ | $10^{6.4}$ |
| | serial mouse number | | | | |
| | 46 | 47 | 48 | 49 | 410 |
| 0.05 ppm group | $10^{5.4}$ | $10^{5.8}$ | $10^{5.6}$ | $10^{5.7}$ | $10^{5.8}$ |

(Simultaneous Administration of 0.03 ppm Chlorine Dioxide)

Next, regarding the case of administration of 10 $LD_{50}$ concentration virus, investigation was made on the effect of simultaneous administration with further reducing the concentration of chlorine dioxide to 0.03 ppm. The result showed that between the group of chlorine dioxide administered group (0.03 ppm) and the control group (0 ppm) no significant difference was found in the number of onsets of influenza (Table 9) or the virus amount in the lung (Table 10).

TABLE 9

Number of mice which died after exposure to 10 $LD_{50}$ virus with simultaneous administration of 0.03 ppm chlorine dioxide (data for 10 mice in each group)

| | days after exposure | | | | | | |
|---|---|---|---|---|---|---|---|
| | 3 | 4 | 5 | 8 | 9 | 10 | 14 |
| 0 ppm group | 0 | 0 | 3 | 7 | 7 | 10 | 10 |
| 0.03 ppm group | 0 | 0 | 3 | 8 | 9 | 10 | 10 |

TABLE 10

Total virus amount in lung tissues on Day 3 after 10 $LD_{50}$ virus exposure with simultaneous administration of 0.03 ppm chlorine dioxide ($TCID_{50}$ values)

| | serial mouse number | | | | |
|---|---|---|---|---|---|
| | 51 | 52 | 53 | 54 | 55 |
| 0 ppm group | $10^{6.1}$ | $10^{6.4}$ | $10^{6.0}$ | $10^{6.1}$ | $10^{6.2}$ |

TABLE 10-continued

Total virus amount in lung tissues on Day 3 after 10 $LD_{50}$ virus exposure with simultaneous administration of 0.03 ppm chlorine dioxide ($TCID_{50}$ values)

| | serial mouse number | | | | |
|---|---|---|---|---|---|
| | 56 | 57 | 58 | 59 | 510 |
| 0.03 ppm group | $10^{6.3}$ | $10^{6.3}$ | $10^{6.1}$ | $10^{6.9}$ | $10^{6.3}$ |

From the above, it has been found that in the cases of influenza virus being present at the concentration of 10 $LD_{50}$, simultaneous administration of 0.03 ppm chlorine dioxide gas is not effective respecting inhibition of influenza in mice.

Hence, it was confirmed that as the influenza onset inhibitory effect in the case of simultaneous administration of chlorine dioxide gas, the chlorine dioxide gas concentration of at least 0.05 ppm or more is effective in case the virus concentration is 10 $LD_{50}$ amount.

Based on the above-described experiments, the chlorine dioxide gas concentration to be maintained at a space can be set in a manner as follows for instance.

In general, when there occurs respiratory viral infectious disease within such a large structure as a theater, an extremely low concentration of virus can be a problem. For instance, even such low concentration as low as 0.02 $LD_{50}$ can cause infection.

In the above situation, the virus concentration in the air is about 1/500 of the above-noted concentration (10 $LD_{50}$/0.02 $LD_{50}$). It follows that the chlorine dioxide concentration required for preventing influenza virus infection is 0.0001 ppm (0.05/500). Therefore, the effect of deactivating virus and preventing infection can be expected with setting of the chlorine dioxide concentration to such low concentration values as above.

(Delayed Administration of 0.08 ppm Chlorine Dioxide Gas)

Next, regarding the 10 $LD_{50}$ concentration virus administered group, the effect of chlorine dioxide gas was investigated for cases of administrating 0.08 ppm chlorine dioxide gas with delays of 5 minutes, 10 minutes and 15 minutes respectively from the start of virus exposure. In the respective cases, the exposure period to the chlorine dioxide gas was 15 minutes.

The object of this experiment is to confirm whether chlorine dioxide gas when administered with a delay is effective for preventing onset of influenza against viruses which have already reached the lungs and proliferated there, that is, whether it has a "treating effect" for influenza or not.

The results are shown in Table 11 and Table 12 below.

TABLE 11

Number of mice which died after exposure to 10 $LD_{50}$ virus with delayed administration of 0.08 ppm chlorine dioxide (data for 10 mice in each group)

| | Days after exposure | | | | | | |
|---|---|---|---|---|---|---|---|
| | 3 | 4 | 5 | 8 | 9 | 10 | 14 |
| 5 minutes delayed administration group | 0 | 0 | 3 | 7 | 7 | 10 | 10 |
| 10 minutes delayed administration group | 0 | 0 | 4 | 9 | 10 | 10 | 10 |

TABLE 11-continued

Number of mice which died after exposure to 10 $LD_{50}$ virus with delayed administration of 0.08 ppm chlorine dioxide (data for 10 mice in each group)

| | Days after exposure | | | | | | |
|---|---|---|---|---|---|---|---|
| | 3 | 4 | 5 | 8 | 9 | 10 | 14 |
| 15 minutes delayed administration group | 0 | 2 | 6 | 10 | 10 | 10 | 10 |

TABLE 12

Total virus amount in lung tissues on Day 3 after 10 $LD_{50}$ virus exposure with delayed administration of 0.08 ppm chlorine dioxide ($TCID_{50}$ values)

| | Serial Mouse Number | | | | |
|---|---|---|---|---|---|
| | 61 | 62 | 63 | 64 | 65 |
| 5 minutes delayed administration group | $10^{6.1}$ | $10^{6.4}$ | $10^{6.0}$ | $10^{6.1}$ | $10^{6.2}$ |
| | Serial Mouse Number | | | | |
| | 71 | 72 | 73 | 74 | 75 |
| 10 minutes delayed administration group | $10^{6.3}$ | $10^{6.3}$ | $10^{6.1}$ | $10^{6.9}$ | $10^{6.3}$ |
| | Serial Mouse Number | | | | |
| | 81 | 82 | 83 | 84 | 85 |
| 15 minutes delayed administration group | $10^{6.8}$ | $10^{6.7}$ | $10^{7.3}$ | $10^{7.7}$ | $10^{7.7}$ |

The results of determination of the total virus amounts showed that the amounts were smaller than expected in spite of the fact that chlorine dioxide gas was administered after lapse of 15 minutes from the virus exposure. Based on this, it is reasoned that delayed administration of chlorine dioxide gas can alleviate the symptoms of influenza.

This result shows that even when influenza virus has already been fixed to the tissue of respiratory organ and proliferated, symptoms of influenza can be restricted with delayed administration of chlorine dioxide gas. This suggests the potential of chlorine dioxide gas achieving treating effect to animals with onset of influenza.

(Experiment of Protein Denaturation with Low Concentration Chlorine Dioxide)

In this embodiment, it has been described based on influenza virus infection experiments using mice that chlorine dioxide gas, even at an extremely low concentration of e.g. 0.05 to 0.1 ppm, is capable of deactivating virus or depriving its infectability.

Such anti-virus effect of chlorine dioxide can be explained based on the following experiment.

In this experiment, glucose-6-phosphate dehydrogenase (referred to shortly as "G6PD" hereinafter) which is an enzyme of yeast was reacted with a low concentration of chlorine dioxide and investigation was made to see how the enzyme activity of G6PD would change.

Chlorine dioxide was dissolved in PBS buffer (20 mM sodium phosphate buffer, pH7, 130 mM NaCl) to final concentrations of 0.1, 1, 10, 100, 1000 μM (0.007, 0.07, 0.7, 7, 70 ppm, respectively if converted into ppm concentration values) (these will be referred to as chlorine dioxide solutions hereinafter). G6PD was dissolved in each chlorine dioxide solution to a final concentration of 80 μg/mL and reaction was allowed to continue at 25° C. for 2 minutes.

The enzyme activity of G6PD was determined by observing absorption of NADPH by a spectral photometer, with using NADP and glucose-phosphoric acid as the substrate. Specific reaction conditions were set according to the manufacturer's (Sigma Corp.) instructions.

The determination results of the enzyme activity are shown in FIG. 1. The concentration values on the horizontal axis are shown as being converted into the unit of ppm. The "specific activity" on the vertical axis represents enzyme activity (unit/mg) per 1 mg of protein The results show that when the chlorine dioxide concentration was 0.07 ppm, there was about 60% reduction (45/71) in the enzyme activity, as compared with the case of chlorine dioxide concentration being 0 ppm.

Therefore, it was found that even a very low concentration of chlorine dioxide as low as about 0.07 ppm can inhibit enzyme activity. This suggests that chlorine dioxide, even at an extremely low concentration range as proposed by the present invention, provides the anti-virus effect of inhibiting enzyme activity.

(Experiment for Confirming Effectiveness of Chlorine Dioxide Against Influenza Virus)

Next, there will be described an experiment conducted to investigate the effect of denaturation of surface proteins present in influenza virus in order to confirm the effectiveness of chlorine dioxide against influenza virus.

On the surface of influenza virus particle, there are two kinds of protein, referred to as hemagglutinin (referred to as HA hereinafter) and neuraminidase (referred to as NA hereinafter).

HA is a protein required at the initial stage of virus infection, that is, required for the virus to bind to the host cell surface and this protein has a function of promoting virus infection. On the other hand, NA is a protein which provides the function of cutting bond between offspring virus proliferated in the host cell and the surface of the host cell, thus separating the virus from the host cell surface. This facilitates diffusion of offspring viruses and spreading of virus infection.

Therefore, with deletion of the HA function, the virus becomes unable to infect or deletion of the NA function can minimize the number of host cells which will be killed by infection. Therefore, it is believed that the infectability of virus will be reduced when at last one of these two proteins loses its function.

Then, investigation was made to see how the functions of the two proteins would change when influenza virus was reacted with chlorine dioxide.

In this experiment, in order to clearly study the denaturing effect of the two proteins relative to chlorine dioxide, the concentration of chlorine dioxide was set so as to range from 2.7 to 21.4 ppm.

Chlorine dioxide was dissolved in PBS buffer (20 mM sodium phosphate buffer to final concentrations of 40, 80, 160, 240 and 320 μM (2.7, 5.4, 10.7, 16.1 and 21.4 ppm, respectively if converted into ppm concentration values) (these will be referred to as chlorine dioxide solutions hereinafter). Influenza virus was dissolved in each chlorine dioxide solution to a final concentration of 77 μg/mL and reaction was conducted on ice for 2 minutes.

After the reaction, titer values of HA were determined by a known blood coagulation reaction test. The results of determination are as shown in Table 13.

TABLE 13

| | Concentration of reacted chlorine dioxide (ppm) | | | | | |
|---|---|---|---|---|---|---|
| | 0 | 2.7 | 5.4 | 10.7 | 16.1 | 21.4 |
| HA titer value | 512 | 256 | 32 | 32 | 16 | 4 |

Further, regarding the case of chlorine dioxide concentration being 5.4 ppm, investigation was made on variation in titer value according to the reaction period. The results of determinations are shown in Table 14.

TABLE 14

| | Reaction period (seconds) | | | | | | | |
|---|---|---|---|---|---|---|---|---|
| | 0 | 5 | 10 | 20 | 30 | 40 | 60 | 120 |
| HA titer value | 256 | 16 | 16 | 16 | 16 | 16 | 16 | 16 |

This suggested that when influenza virus is reacted with chlorine dioxide, HA is denatured immediately to lose its function.

Table 15 shows the determination results of NA titer values.

TABLE 15

| | Concentration of reacted chlorine dioxide (ppm) | | | | | |
|---|---|---|---|---|---|---|
| | 0 | 2.7 | 5.4 | 10.7 | 16.1 | 21.4 |
| NA titer value | 38.8548 | 37.3824 | 32.7322 | 18.7712 | 10.4366 | 7.2408 |
| standard deviation | 0.698112 | 1.59382 | 1.095355 | 0.677734 | 0.265636 | 0.118774 |

This suggested that when influenza virus is reacted with chlorine dioxide, NA is denatured immediately to lose its function.

Based on the above, it was confirmed that chlorine dioxide reduces the infectability of influenza virus.

[Other Embodiments]

In the above embodiment, as an example of the "space", a place where virus is present, such a location as a theater where humans enter/exit was described. However, the present invention is not limited thereto. A location where humans enter/exit can be in a liquid such as a swimming pool, bath, etc.

Further, in the foregoing, animals were described as living creatures as the subjects. However, the present invention is not limited thereto. The invention can be applied to plants which have the possibility of being infected with floating virus.

INDUSTRIAL APPLICABILITY

The present invention can be used in a method of controlling floating virus infection.

BRIEF DESCRIPTION OF DRAWING

[FIG. 1] a view showing determination of enzyme activity of G6PD reacted with chlorine dioxide.

The invention claimed is:

1. A method of controlling respiratory virus infection comprising the step of:

supplying chlorine dioxide gas into air of a space that can assume a closed state or an opened state, where respiratory virus that has hemagglutinin and/or neuraminidase on a surface of viral particle thereof can be present, at a concentration which allows an animal that can be infected with the respiratory virus to live or stay, but deactivates the virus, wherein the concentration of the chlorine dioxide gas in the air of the space is from 0.0001 ppm to 0.1 ppm.

2. The method according to claim 1, wherein the respiratory virus comprises influenza virus.

3. A method of controlling respiratory virus infection comprising the step of:

supplying chlorine dioxide gas into air of a space that can assume a closed state or an opened state, where respiratory virus that has hemagglutinin and/or neuraminidase on a surface of viral particle thereof can be present, at a concentration which allows an animal that can be infected with the respiratory virus to live or stay, but can treat infection of the animal with the virus, wherein the concentration of the chlorine dioxide gas in the air of the space is from 0.0001 ppm to 0.1 ppm.

4. The method according to claim 3, wherein the respiratory virus comprises influenza virus.

5. A method of controlling respiratory virus infection comprising the step of:

supplying chlorine dioxide gas into air of a space that can assume a closed state or an opened state, where respiratory virus that has hemagglutinin and/or neuraminidase on a surface of viral particle thereof can be present, at a concentration which allows an animal that can be infected with the respiratory virus to live or stay, but can alleviate a symptom of a viral disease of the respiratory virus in the animal infected with the virus, wherein the concentration of the chlorine dioxide gas in the air of the space is from 0.0001 ppm to 0.1 ppm.

6. The method according to claim 5, wherein the respiratory virus comprises influenza virus.

7. A method of controlling respiratory virus infection comprising the step of:

supplying chlorine dioxide gas into air of a space that can assume a closed state or an opened state, where respiratory virus that has hemagglutinin and/or neuraminidase on a surface of viral particle thereof can be present, at a concentration which allows an animal that can be infected with the respiratory virus to live or, but can treat the animal infected with the virus in which a viral disease of the respiratory virus has already occurred, wherein the concentration of the chlorine dioxide gas in the air of the space is from 0.0001 ppm to 0.1 ppm.

8. The method according to claim 7, wherein the respiratory virus comprises influenza virus.

* * * * *